United States Patent [19]

Scanlon

[11] Patent Number: 5,515,865

[45] Date of Patent: May 14, 1996

[54] SUDDEN INFANT DEATH SYNDROME (SIDS) MONITOR AND STIMULATOR

[75] Inventor: Michael Scanlon, Silver Spring, Md.

[73] Assignee: The United States of America as represented by the Secretary of the Army, Washington, D.C.

[21] Appl. No.: 231,081

[22] Filed: Apr. 22, 1994

[51] Int. Cl.$^6$ ..................................................... A61B 5/05
[52] U.S. Cl. ........................................... 128/721; 128/774
[58] Field of Search ..................................... 128/721, 722, 128/724, 782, 671; 340/573

[56] References Cited

U.S. PATENT DOCUMENTS

| | | | |
|---|---|---|---|
| Re. 32,180 | 6/1986 | Lewiner et al. | |
| 3,547,106 | 12/1970 | Bornmann | 128/721 |
| 3,972,320 | 8/1976 | Kalman | |
| 4,146,885 | 3/1979 | Lawson, Jr. | 128/721 |
| 4,438,771 | 3/1984 | Friesen et al. | |
| 4,619,270 | 10/1986 | Margolis et al. | 128/721 |
| 4,630,614 | 12/1986 | Atlas | 128/721 |
| 4,694,839 | 9/1987 | Timme | 128/721 |
| 4,813,427 | 3/1989 | Schlaefke et al. | 128/721 X |
| 4,862,144 | 8/1989 | Tao | 390/573 |

OTHER PUBLICATIONS

"Monitoring of Breathing with a Segmental Air Filled Mattress" by Gunderson et al., *Medical and Biological Engineering*, vol. 9, pp. 541–547, 1971.

*Primary Examiner*—Sam Rimell
*Attorney, Agent, or Firm*—Freda L. Krosnick; Charles H. Harris

[57] ABSTRACT

A movement and sound monitor and stimulator which is particularly useful for preventing death in human infants from sudden infant death syndrome is disclosed. The movement and sound monitor and stimulator has a base member which may be a fluid-filled sensing pad for supporting the infant or other animate object which is being monitored and a transducer positioned for detecting movement or acoustic activity (e.g., heartbeat, breathing) of the object on the base member to provide an output signal in response to forces applied thereto which are generated by such movement. A circuit is connected to monitor the output signal from the transducer and activates a stimulator which is operable to provide movement to the base member to stimulate movement in the object when output from the transducer to the circuit corresponds to no movement from the object. The transducer may be a pressure transducer in fluid communication with the fluid interior of the sensing pad. In the alternative, a piezo-electric sheet operatively connected to a surface of the sensing pad to detect such movement as well as movement cessation. The circuit may also be connected to an alarm which can provide an audible or visual indication to third parties when there is no movement from the object.

17 Claims, 3 Drawing Sheets

SUDDEN INFANT DEATH SYNDROME (SIDS) MONITOR AND STIMULATOR

TECHNICAL FIELD

The present invention relates to a movement monitor suitable for detecting movement and, more particularly, to a movement monitor suitable for monitoring and stimulating/resuscitating a human or other living organism's breathing movement.

BACKGROUND ART

Sudden Infant Death Syndrome (SIDS) is a medical condition whereby an infant suddenly stops breathing, leading to the eventual death of the infant. Although the cause and initial symptoms of SIDS is not completely understood, it is felt that a child can be awakened from the SIDS condition.

Unfortunately, many currently available baby monitors are usually only provided with a microphone/transmitter and a receiver/speaker, enabling the parents to monitor baby noises such as crying, coughing, sneezing and sniffling. If the parents do not hear anything, they assume the baby is sleeping, and therefore do not need to check in on the child. Unfortunately, in some tragic situations, the absence of baby noises can be deadly to the child.

Consequently, other devices are known in the art which monitor breathing or baby motion to sound an alarm in the absence of such breathing or motion. U.S. Pat. No. 4,438,771, for example, discloses an apparatus for detecting the cessation of body movement by detecting the voltage produced by the movement of the charge on the body attributable to such movement. This is accomplished by a passive contactless conductive pad which is spaced from the body and in which a potential is induced by the movement of the body through the movement of the charge on the body. This potential is amplified and an alarm indication device responds to the amplified potential to produce an alarm when the output of the amplifier is below a predetermined value for a predetermined period of time. With this device, an alarm indication is provided to the parents which then necessitates a proactive role by the parents to start the artificial respiratory procedures necessary to induce continued rhythmic breathing.

Another movement monitor is disclosed in U.S. Pat. No. 4,862,144 wherein the apparatus disclosed therein monitors motion and breathing by transmitting pressure signals to a pad by means of a strap secured around the person's body to facilitate forced transmission. The present or absence of breathing motion is monitored and logic circuitry can be actuated to provide an alarm should the output from the transducer sense no movement from the moving object. Again, however, the alarm necessitates a proactive role on the part of parents or third parties to try to stimulate breathing of the child upon receipt of the alarm.

SUMMARY OF THE INVENTION

It is accordingly one object of the present invention to detect the absence of breathing movement of a living organism and then attempt to stimulate breathing movement with at least some type of physical movement applied to the organism.

Another object is to monitor for the absence of breathing by the use of passive sensors, and preferably without any restraint devices and without impeding normal movement of the organism.

Yet another object is to provide a movement monitor and stimulator suitable for use with adults or other respiring animals.

Still a further object is to stimulate movement of a living organism upon breathing or heartbeat cessation while optionally providing an alarm to alert and solicit professional or parental assistance in the performance of further lifesaving procedures subsequent to the initial physical stimulus measures provided prior to response to the alarm.

A sound or movement monitor and stimulator, in accordance with the present invention, comprises a base member for supporting an object in which movement is being monitored, and a transducer positioned for detecting acoustic activity or movement of the object on the base member. The transducer provides an output signal in response to forces applied thereto which are generated by and representative of said activity or movement. A circuit is connected to monitor the output signal from the transducer. A stimulator is connected to the circuit and is operable to provide at least physical movement to the base member or directly to the object to stimulate movement in the object when the transducer output to the circuit corresponds to no movement or, optionally, abnormal movement (below a predetermined threshold) from the object.

The "transducer," as used in this specification, may be a microphone or similar means for picking up acoustic signals (e.g., heartbeat) and/or varying pressure signals.

Preferably, in the preferred embodiment, the stimulator generates vibratory, oscillatory or shaking movement of the base member in horizontal and/or vertical directions. The stimulator also preferably generates an audible noise to stimulate the object acoustically.

The base member, such as a sensor pad, preferably has characteristics sufficient to transmit to the transducer the movement from the object in the form of at least one of breathing, heart and motion sounds of the object. In the preferred embodiment, the base member is a fluid-filled mattress and the transducer is a pressure transducer arranged in fluid communication with the internal fluid volume of the mattress such that forces applied to the mattress by the object cause pressure changes which are detected by the pressure transducer. The pressure transducer then provides an output proportional to the pressure changes.

The mattress may be a sensor pad having top and bottom surfaces which are sufficiently rigid so as to facilitate transmission of pressure fluctuations from the object to the transducer.

In accordance with another embodiment of the invention, the transducer and the base member include a piezo-electric sheet which is operable to create a charge output when stressed or deformed by movement of the object and which is connected to the circuit to supply a voltage thereto to generate the output signal.

In accordance with another feature of the invention, the piezo-electric sheet may be operably positioned adjacent a sensor pad containing both a fluid and top and bottom surfaces which have characteristics sufficient for transmitting movement of the object to the piezo-electric sheet.

The invention may further comprise an alarm which is activated by the circuit when the output from the transducer corresponds to no movement (and/or absence of cardiopulmonary sounds) from the object.

The movement stimulator preferably includes means for shaking the base member to stimulate movement of the object. Such shaking means may comprise a piston and cylinder arrangement, a solenoid, or an eccentric (motor with an unbalanced mass on its shaft).

Still other objects and advantages of the present invention will become readily apparent to those skilled in this art from the following detailed description, wherein only the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

BEST MODE FOR CARRYING OUT THE INVENTION

Figure 1:
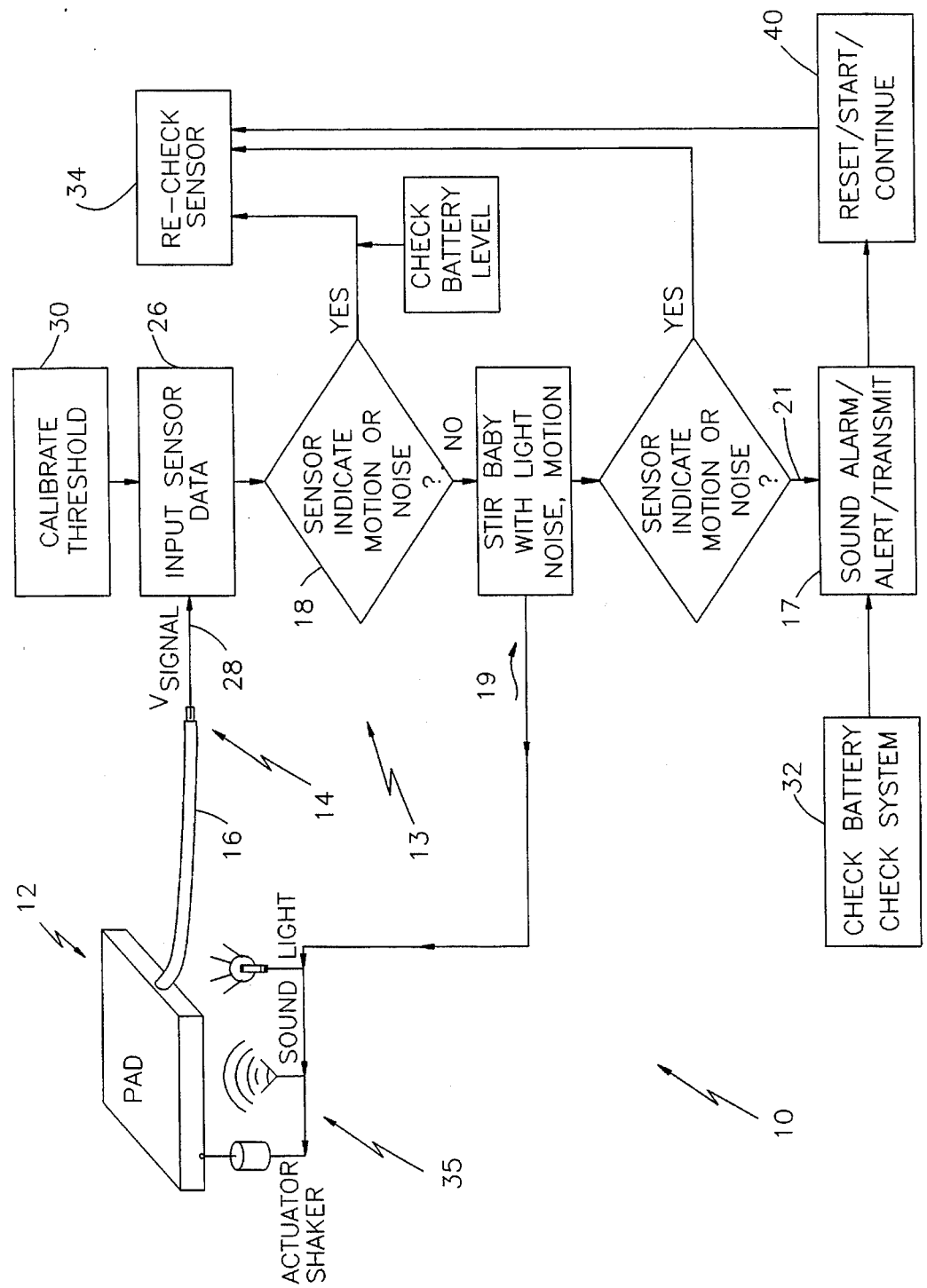
FIG. 1 is an illustration, partly in schematic form, of a presently preferred embodiment of a sudden infant death syndrome monitor and stimulator according to the present invention.

FIG. 1 is an illustration of a preferred embodiment of a sudden infant death syndrome monitor and stimulator, generally designated with reference numeral 10, wherein a sensor pad 12 placed beneath a child in a crib, incubator, bed or the like, is connected to a sensing and monitoring system 13 to monitor the pressure fluctuations of the fluid-filled pad such as may be caused by the child's breathing, heart and motion sounds. Since water is an excellent transmitter of sound, the preferred embodiment contemplates the use of a pressure transducer 14, connected to the water chamber in pad 12 through hose 16 or the like, which is provided to continuously sense the fluid for pressure fluctuations. The pressure transducer 14 may be a microphone, hydrophone, accelerometer, a fluidic sensor, etc. Once the signal level has dropped below a pre-set threshold for a predetermined period of time (which may be medically and experimentally determined), indicating that the child is not breathing or not present, an alarm 17 may sound to alert professional or parental authorities. In accordance with the present invention, and independent from alarm actuation, monitor and system 10 uniquely features control circuitry and logic 18 used to actuate a stimulating means 19 and 35 connected either to pad 12 in order to shake or otherwise move the pad or the baby directly to awaken or stimulate breathing.

Preferably, while monitoring the sensor 14 for signs of improvement, the system 10 would transmit or send an alert signal 21 for help. If the attempt to stir the baby was successful, the alert signal 21 may not be necessary, and the system 10 can be designed to continue to monitor the baby as usual without transmitting an alarm to parents or attendants.

Figure 2:
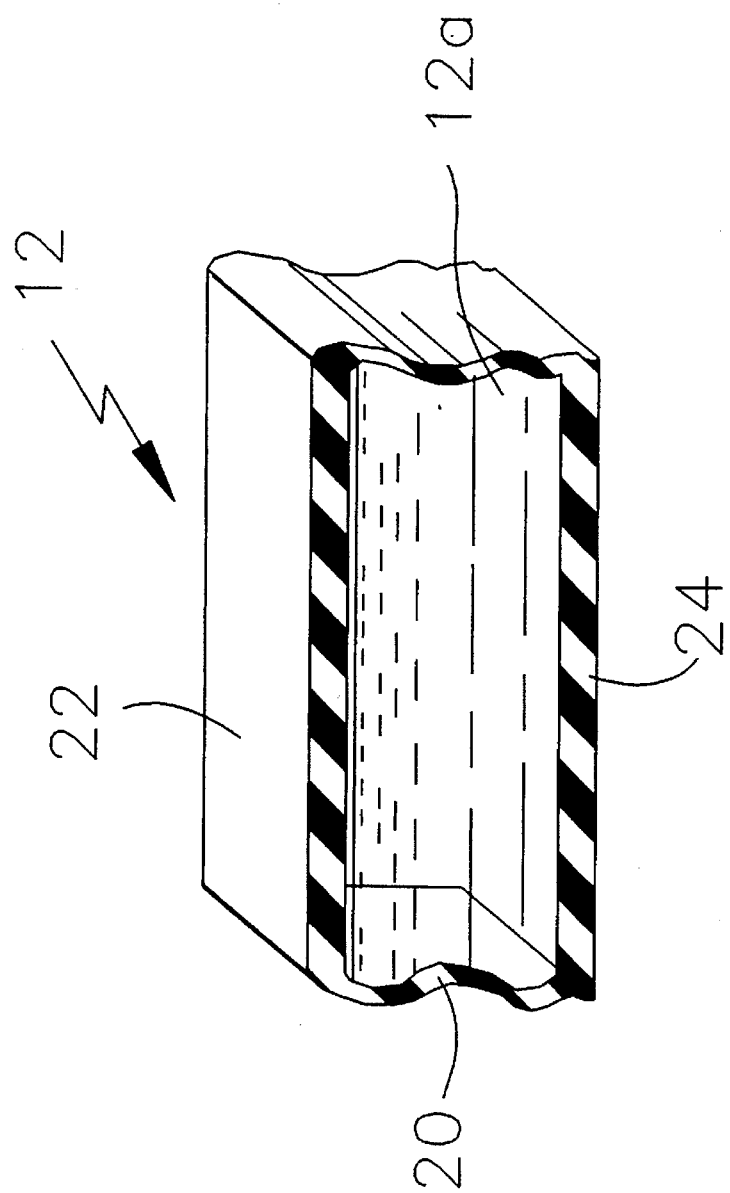
FIG. 2 is a detail sectional view of a exemplary sensor pad that may be used to practice the present invention.

The sensor pad 12, as best depicted in FIG. 2, is characterized by a mattress formed with an interior fluid chamber 12a (preferably containing water or air) having flexible side walls 20 and top and bottom walls 22 and 24 in a design which may be similar to a hot water bottle. These top and bottom walls 22,24 are preferably rigid or semi-rigid so as not to absorb pressure fluctuations. The rigidity of the walls 22,24 must facilitate acoustic transmission but are preferably not flexible enough to conform to the child's face and thereby restrict breathing.

The pad 12 may be formed with conduits (not shown in detail) within the pad interior 12a to ensure that pressure fluctuations are transmitted efficiently to the pressure transducer sensing element 14 which fluidly communicate with the pad interior or the conduits through hose 16 as discussed above.

An exemplary pad, hose and pressure transducer arrangement which may be used to practice the present invention is depicted in FIG. 5 of U.S. Pat No. 4,862,144, issued Aug. 29, 1989, for a movement monitor. The above-mentioned figure and related description in this '144 patent is hereby incorporated by reference herein.

In accordance with other embodiments that may be used to practice the present invention, the sensor pad 12 need not necessarily be fluid-filled. For example, piezo-electric sheet material (not shown in detail) can be used as the sensing element with or without the fluid-filled pad 12. Piezo-electric films create a charge output when stressed or deformed. When converted to a voltage, this charge output could be monitored in the same way as pressure transducer 14. A sheet or multiple strips of piezo-electric film material would be relatively inexpensive and would not produce an electromagnetic field or create a shock hazard since it does not have enough voltage applied to it. If used in combination with a fluid-filled pad 12, the fluid-filled pad may increase the performance of the piezo-electric film by allowing greater deformation of the film, as opposed to attachment of the piezo-electric film to top and/or bottom surfaces of a flexible, nonfluid-filled pad (not shown in detail).

The electronic circuitry 18,19,26 associated with system 10 is relatively simple and the selection and design of such circuitry will be obvious to an electrical engineer of ordinary skill upon review of this specification. Briefly, a voltage comparator 26 constantly monitors the output signal 28 from pressure transducer 14. If signal 28 falls below a certain threshold level (calibrated at step 30), appropriate timing and alarm circuits 18,19 which may operate a gating logic circuit are used to activate the visual and/or audible alarm 17. The various circuit means, preferably battery operated as at 32, may be identical or similar to the disclosed circuitry means in FIGS. 9 and 11 of the aforesaid U.S. Pat No. 4,862,144, such figures and relevant figure descriptions therein being incorporated by reference herein. Other types of voltage comparator circuits, level detectors, and change-in-state circuits as well known in the art may also be utilized. Additional components such as filters or digital signal processors as known in the art may be used to remove unnecessary noise and enhance or identify the signals of interest in step 18.

Once the danger condition (such as the absence of breathing, heart movement, etc.) is detected, the circuitry means of this invention is also advantageously connected to a noise or vibrator or other means, generally designated by reference numeral 35 in FIG. 1, to apply a stimulus to the pad 12. Preferably, any stimulus applied to pad 12 includes at least active shaking or other type of movement applied to the pad so as to physically move the child to reactivate breathing.

After the stimulus has been applied for a predetermined length of time as determined by the timing circuit, the circuit may re-set as at 34 to the normal monitoring condition to evaluate whether the stimulus is effective. If not effective, the stimulus may be reapplied and the alert sounded or re-sounded. With the use of a transmitter 54 (see FIG. 3), parents/doctors could also check the signal being generated.

The system 10 may also feature a sensor sensitivity adjustment or an alarm threshold adjustment which would calibrate the system to its environment. Adjusting the threshold of the system 10 to respond to the "baby not present" condition, would calibrate the device to not respond when the baby is placed on the sensor pad 12. When the baby is present and breathing on the pad 12, the output level would be higher than room noise. If this level drops to room noise for a predetermined length of time, the system 10 would either sound an alarm or attempt to stir the baby. If the baby is successfully stirred, the alarm is re-set and continues to monitor.

Figure 3:
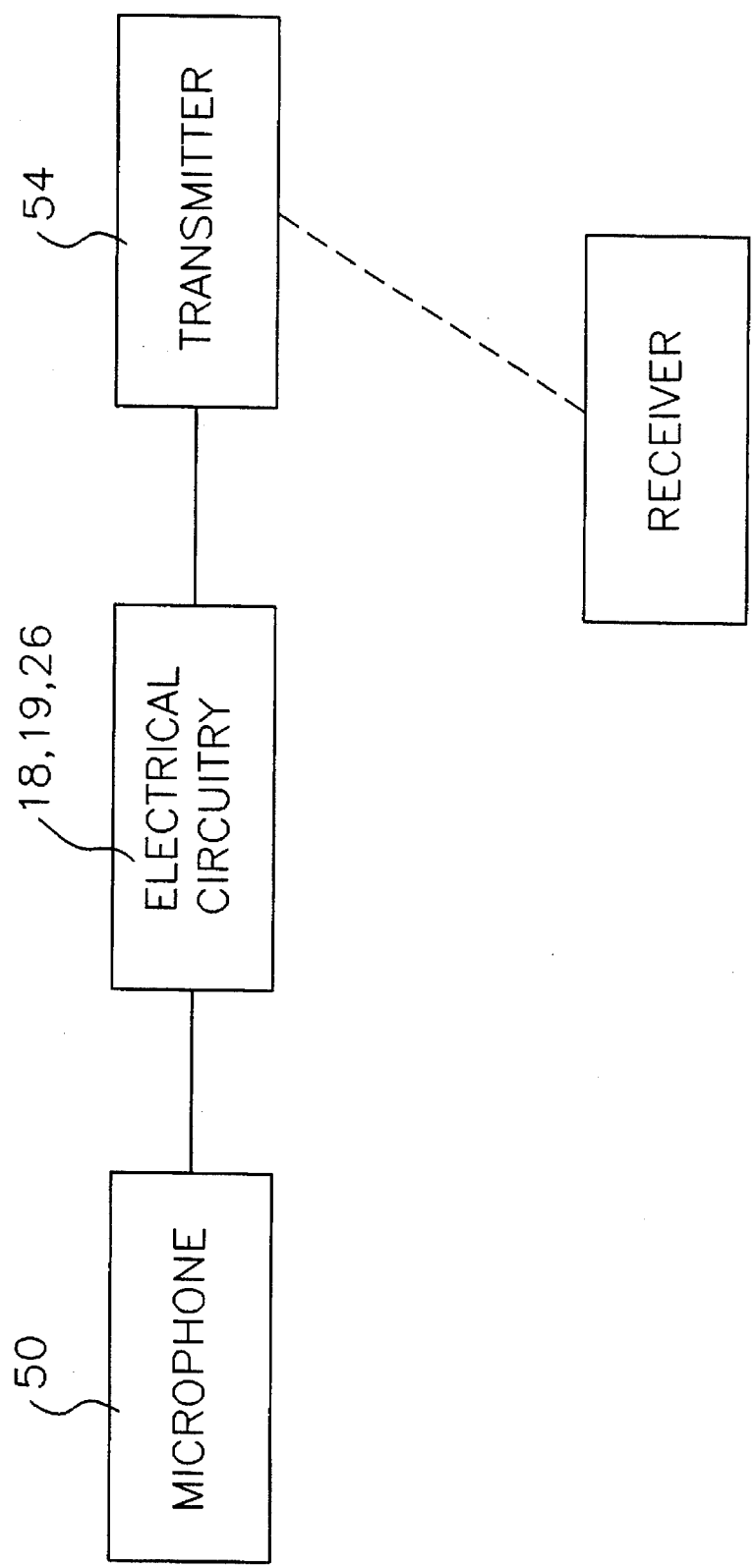
FIG. 3 shows in schematic form a transmitter/receiver arrangement according to the present invention.

As mentioned above, the sensor 14 in the fluid-filled system may be a piezo-electric or ceramic hydrophone, similar to those used by the U.S. Navy in sonar applications. The synergistic combination of different sensor technologies placed inside, on, or near the sensor pad 12 can enhance reliability of system performance. Using multiple sensors in an array configuration can also improve signal to noise ratio (SNR) and create focussed zones of sensing. Other one or more sensor technologies may also be used as will occur to one of ordinary skill. When installed at the edge of the fluid pad 12, or in a fluid-filled tube 16 extending from the pad and terminating in a diaphragm which transmits pressure to the sensor, the sensor would generate a voltage output corresponding to any pressure fluctuations within the fluid. These pressure fluctuations may be transmitted to conduits within the pad to ensure that such fluctuations are transmitted efficiently to the sensing element. Motion of the baby's torso during breathing will be transmitted to the fluid through the walls 22 and/or 24 and detected by the sensor 14. It is also possible to detect, as verified through experimentation, heartbeat and breathing through the water pad. Such heartbeat and breathing sounds, in addition to motion noises, can be clearly detected with a transducer such as microphone 50, as set forth in FIG. 3, and tend to be significantly higher in amplitude than ambient noise. FIG. 3 shows in schematic a basic transmitter/receiver arrangement having a microphone 50 for detecting sound or acoustic activity. Electrical circuitry 18, 19, 26 may be connected to the microphone and a transmitter 54. A receiver 54 may receive electrical signals from the transmitter to notify parents or doctors of the condition of the animate object. Of course, movement activity may also be monitored by the transmitter/receiver arrangement.

Once the danger condition has been sensed for the proper duration as determined by the timing circuit, an attempt to stir the baby must be made immediately. As mentioned above, such a stimulus could be created by a loud acoustic source, such as a beeper, siren, or bell. Preferably, however, a vibrating or other type of movement generating source 35 is used to transmit vibration and movement through the fluid pad 12 or directly to the frame of the bed or cradle in order to shake and restore breathing or wake the baby. Bright light may also assist in waking the baby. Parents or doctors can be notified through common methods, such as audio alarms, flashing lights, beepers or other transmitter devices as mentioned above. Immediate action by those present can significantly improve treatment.

The system 10 also features a low battery indicator 32 (e.g., light or sound), and system performance test button 40. As mentioned above, a sensor sensitivity adjustment or an alarm threshold adjustment is used to calibrate the system to its environment.

The unique system 10 in accordance with the present invention has the potential to save the lives of many infants that are afflicted with sudden infant death syndrome (SIDS). Parents and medical staff will be able to relax somewhat in the knowledge that the baby is being constantly monitored for normal breathing.

It will now occur to one of ordinary skill in the art from reviewing this specification that, with slight modification, this invention may also be used for controlling general apnea, stop snoring, or sensing the onset of sleep for drivers of automobiles (e.g., by monitoring a slow down in heart rate or breathing).

In accordance with another feature of this invention, it will now be appreciated by one of ordinary skill that the circuitry means 17 may also be used to transmit the data being monitored to parental or medical authorities and not merely provide a warning or alert indication. Data representative of breathing rate, for example, or perhaps heart sounds, may be transmitted and therefore monitored at a remote location.

Another unique feature of this invention which may be achieved through the vibrating means or shaker means connected to the pad 12 and operated by the circuitry means 19, is the ability to operate the shaker in a quieter, soothing amplitude mode to either assist the baby in falling asleep or to quiet the baby should it wake up unexpectedly. Appropriate circuitry modifications to the detection circuitry will be obvious to one of ordinary skill based upon this disclosure.

Upon detection of no movement or acoustic activity in the animate object, it is also possible to re-stimulate such movement or acoustic activity by means of electrical shock.

The circuitry employed in the preferred embodiment of this invention may also include outputs corresponding to heartbeat and breathing rates, as well as a clock for measuring elapsed time since a last warning, number of incidents, time of cessation of movement or acoustic activity, false alarms, etc.

A pressure switch can be used to turn the system off when the baby is removed from pad 12 to prevent alarms from going off without necessarily requiring the parents to turn the system off manually before removing the child. However, this feature may not be desirable if the pad is being used as a security device.

It should be understood that "baby waterbeds" are now available as commercial products. Therefore, the sensor and shaker mechanisms as well as the alarms identified hereinabove may be an attachment to existing waterbeds as noted above.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

I claim:

1. A movement and sound monitor and stimulator, comprising:

(a) a base member for supporting an animate object and including a liquid-filled mattress;

(b) a movement and sound transducer positioned for detecting movement activity and acoustic activity of the animate object on said base member, said transducer providing an output signal in response to forces applied thereto which are generated by and representative of said movement and acoustic activity, wherein said base member is configured so said acoustic activity from the animate object in the form of at least one of breathing, heart and motion sounds of the animate object is transmitted to said transducer;

(c) a circuit connected to said transducer and adapted to monitor said output signal from said transducer;

(d) a stimulator connected to said circuit and being operable to provide at least physical movement to said base member to stimulate movement activity or acoustic activity in the animate object when the output signal from said transducer to said circuit corresponds to no movement activity and no acoustic activity from the animate object.

2. The movement and sound monitor and stimulator of claim 1, wherein said stimulator generates vibratory movement of said base member.

3. The movement and sound monitor and stimulator of claim 1, wherein said transducer includes a pressure transducing element arranged in communication with the liquid within said mattress such that forces applied to said mattress by said object cause pressure changes which are detected by said pressure transducing element, said pressure transducing element providing an output proportional to the pressure changes.

4. The movement and sound monitor and stimulator of claim 3, wherein said mattress is a sensor pad having top and bottom surfaces which are sufficiently rigid so as to facilitate transmission of pressure fluctuations from the object to said transducer.

5. The movement and sound monitor and stimulator of claim 1, wherein one of said transducer and said base member includes a piezo-electric sheet operable to create a charge output when stressed or deformed by movement of the object and connected to said circuit to supply a voltage thereto to generate said output signal.

6. The movement and sound monitor and stimulator of claim 5, wherein said mattress has top and bottom surfaces, said piezo-electric sheet is operatively positioned adjacent said mattress, said mattress is configured so movement of said object is transmitted to said piezo-electric sheet.

7. The movement and sound monitor and stimulator of claim 1, further comprising an alarm actuated by said circuit when said output from said transducer corresponds to at least one of no movement from the object and absence of predetermined acoustic signals.

8. The movement and sound monitor and stimulator of claim 1, wherein said stimulator includes means for shaking said base member to stimulate movement of the animate object.

9. The movement and sound monitor and stimulator of claim 5, wherein said liquid contained in said mattress is water.

10. A movement and sound monitor and stimulator, comprising:

a liquid-filled sensor pad adapted to support an animate object and receive sounds from the animate object;

a movement and sound transducer monitoring movement and sounds of the animate object on said sensor pad, said transducer including sound transducing means for receiving sounds emitted by the animate object and transmitting electrical signals corresponding to the sounds;

a circuit connected to said transducer and adapted to receive the electrical signals corresponding to the sounds from said transducer;

a physical stimulator connected to said circuit and adapted to physically move said sensor pad and the animate object.

11. The movement and sound monitor and stimulator of claim 10, wherein said movement and sound transducer includes a piezo-electric sheet attached to said sensor pad.

12. The movement and sound monitor and stimulator of claim 11, further comprising an alarm connected to said circuit, said alarm including a sound emitting element.

13. The movement and sound monitor and stimulator of claim 12, wherein said alarm further includes a light emitting element.

14. An acoustic monitoring system comprising:

a liquid-filled sensor pad adapted to support an animate object and receive acoustic signals from the animate object;

acoustic transducing means for monitoring and converting the acoustic signals within said sensor pad to electrical signals corresponding to the acoustic signals;

a circuit connected to said acoustic transducing means and adapted to receive the electrical signals corresponding to the acoustic signals from said acoustic transducing means;

a transmitter located at a first position and connected to said circuit, said transmitter configured to transmit signals corresponding to the acoustic signals of the animate object;

a receiver located at a second position spaced apart from said first position and configured to receive signals from said transmitter.

15. The acoustic monitoring system of claim 14, further comprising a physical stimulator connected to said circuit and adapted to physically move said sensor pad and the animate object.

16. The acoustic monitoring system of claim 15, further comprising an alarm connected to said circuit, said alarm including a sound emitting element.

17. The acoustic monitoring system of claim 16, wherein said alarm further includes a light emitting element.

* * * * *